(12) United States Patent
Deshpande et al.

(10) Patent No.: US 9,580,397 B2
(45) Date of Patent: Feb. 28, 2017

(54) PROCESS AND APPARATUS FOR PRODUCING DIVINYLARENE DIOXIDE

(71) Applicant: Blue Cube IP LLC, Midland, MI (US)

(72) Inventors: Kishori Deshpande, Midland, MI (US); David Jean, Midland, MI (US); Jianping Zeng, Midland, MI (US); Ravindra S. Dixit, Midland, MO (US); David H. West, Midland, MI (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

(21) Appl. No.: 14/899,667

(22) PCT Filed: Jun. 3, 2014

(86) PCT No.: PCT/US2014/040587
§ 371 (c)(1),
(2) Date: Dec. 18, 2015

(87) PCT Pub. No.: WO2014/204639
PCT Pub. Date: Dec. 24, 2014

(65) Prior Publication Data
US 2016/0130242 A1   May 12, 2016

Related U.S. Application Data

(60) Provisional application No. 61/836,867, filed on Jun. 19, 2013.

(51) Int. Cl.
*C07D 301/12* (2006.01)
*B01J 19/24* (2006.01)

(52) U.S. Cl.
CPC .............. *C07D 301/12* (2013.01); *B01J 19/24* (2013.01); *B01J 2219/00051* (2013.01); *B01J 2219/24* (2013.01)

(58) Field of Classification Search
CPC ..................................................... C07D 301/12
USPC .......................................................... 549/531
See application file for complete search history.

(56) References Cited

U.S. PATENT DOCUMENTS

| | | |
|---|---|---|
| 2,977,374 A | 3/1961 | Starcher |
| 8,674,122 B2 | 3/2014 | Ripplinger et al. |

FOREIGN PATENT DOCUMENTS

| | | |
|---|---|---|
| WO | 2011/084687 | 7/2011 |
| WO | 2012/082482 | 6/2012 |

*Primary Examiner* — Taofiq A Solola
(74) *Attorney, Agent, or Firm* — Polsinelli PC

(57) ABSTRACT

A process for preparing a divinylarene dioxide including the steps of: (a) feeding one or more feed streams of the following reactants into a reactor system: (i) at least one divinylarene, (ii) at least one oxidizing agent, and (iii) at least one solvent to form a reaction mixture in the reactor system; (b) continuously reacting together the one or more feed streams of the reactants of step (a) in the reaction mixture; and (c) controlling heat removal of the reaction mixture as the reactants of step (b) react together; wherein the heat removal is sufficient to provide a residence time of the reactants in the reaction mixture of less than about 180 minutes residence time of the reactants in the reaction step (b); and an apparatus for preparing a divinylarene dioxide.

12 Claims, 3 Drawing Sheets

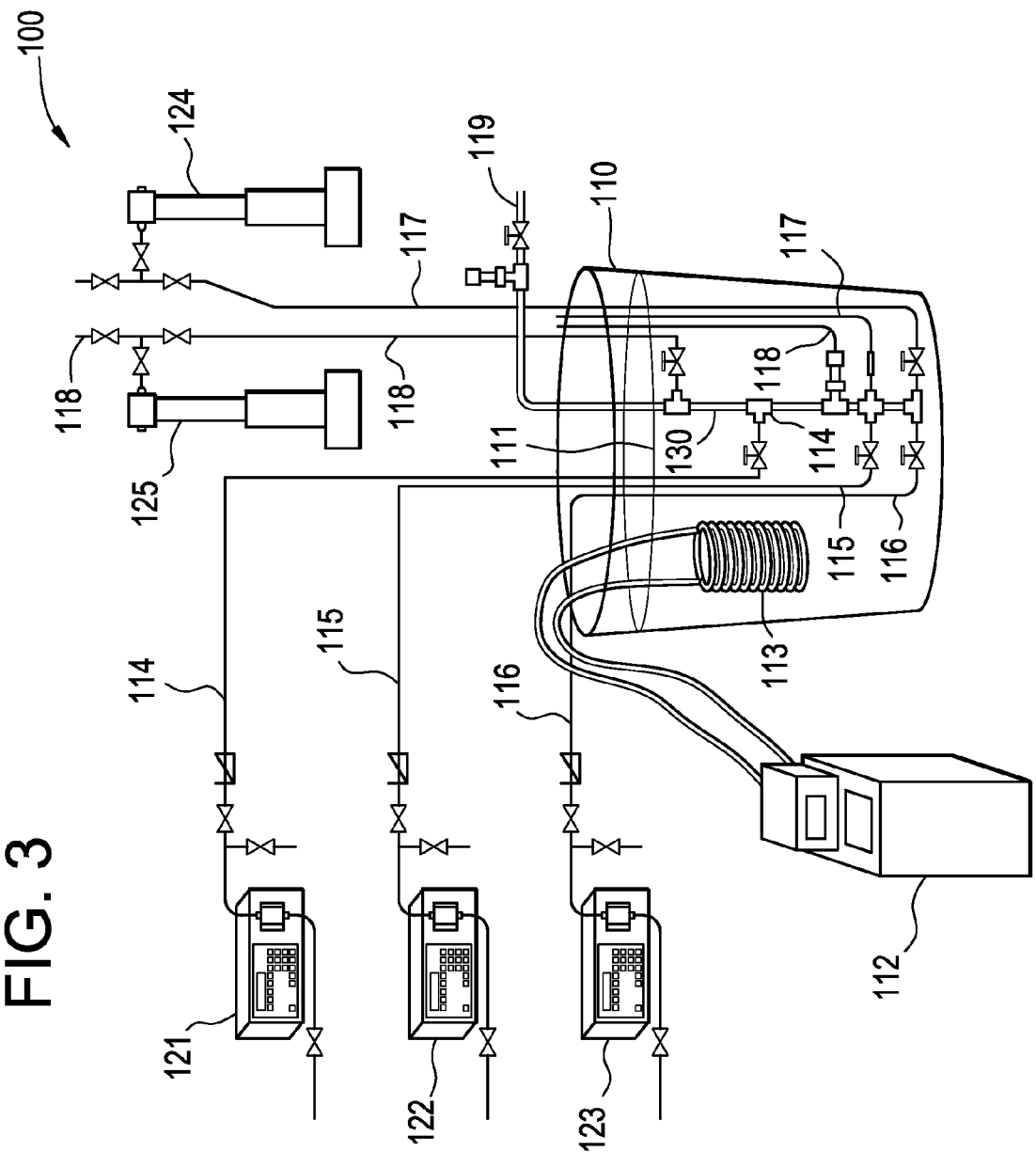

PROCESS AND APPARATUS FOR PRODUCING DIVINYLARENE DIOXIDE

CROSS-REFERENCE TO RELATED APPLICATIONS

This application claims priority from provisional application Ser. No. 61/836,867, filed Jun. 19, 2013, which is incorporated herein by reference in its entirety.

FIELD

The present invention is related to a process and apparatus for producing a divinylarene dioxide.

BACKGROUND

Divinylarene dioxide, such as divinylbenzene dioxide (DVBDO), an oxirane compound, advantageously can have a 1,000 times lower viscosity (for example, 8 mPa-s-12 mPa-s) than conventional epoxy resin compounds; and divinylarene dioxide resins are beneficially used in many applications including for example coatings, laminates and adhesives. Therefore, it would advance the art to provide a process for preparing an oxirane compound at high yields and high selectivity on a commercial scale.

Currently known processes for producing an oxirane compound include a batch, a semi-batch process or a continuous process. Known batch or a semi-batch process for producing a divinylarene dioxide resin, such as DVBDO, have the disadvantage of, for example, involving highly exothermic oxidation of divinyl benzene (DVB) with a net heat of reaction of up to 606 kJ/mol and an adiabatic temperature rise up to 523 K for a feed stream composition containing up to 13 weight percent (wt %) DVB. The reaction exotherm of the semi-batch process, for example, is addressed by slow addition of the reactants over 4-5 hours resulting in a long processing time of up to 6 hours; and hence, the productivity of the process is considered low. For example, the yield of DVBDO produced in a 15.14 cubic meter batch reactor is about 150 kg/hour.

U.S. Pat. No. 2,977,374 discloses a continuous process for preparing oxirane compounds; and the advantages of a continuous process over a batch synthesis. WO/2012/082482 and WO 2011/084687 A1 disclose a process to make divinylarene dioxide from divinyl benzene in the presence of a peroxycarboximidic acid agent. WO/2012/082482 mentions using a process including a combination of a continuous stirred tank reactor (CSTR) and a plug flow reactor (PFR) for continuously processing divinylbenzene dioxide.

SUMMARY

One objective of the present invention is to provide a continuous process that significantly reduces processing time; and improves the yield and selectivity of an oxirane product made by the process. For example, in one embodiment, the expected saving in processing time for producing an oxirane product using the process of the present invention can include a time savings of 30 minutes or more and up to a 12-fold decrease in residence time.

Another objective of the present invention is to provide a continuous process that can be scaled-up rapidly for commercial use. The capacity of the continuous process of the present invention can be easily expanded to meet market demand for an oxirane product such as DVBDO. A continuous process would be easier to scale-up and enable rapid capacity expansion to match product demand growth.

Still another objective of the present invention is to provide a continuous tubular reactor process that can improve yield and selectivity of an oxirane product through better thermal management and controlled residence time.

And, yet another objective of the present invention is to provide a reactor design including a feed distribution design adapted to ensure pH control and thereby improving the yield and the selectivity of the oxirane product made by the process of the present invention.

Another important objective of the present invention is to provide a method and means for controlling heat removal from the reaction process such as to avoid a runaway reaction. i.e., an autocatalyzed, self-heating, exothermic reaction of an epoxide resulting in an uncontrolled temperature and/or a pressure increase. The present invention advantageously reduces the risk of a runaway reaction by operating at a temperature and a residence time where a runaway reaction has a lower probability of occurring.

To meet the above objectives, the present invention is directed to a novel continuous process for preparing a divinylarene dioxide that provides improved yield and selectivity; and in a preferred embodiment, to a novel reactor design for such process including for example a distributed feed with a CSTR, a PFR, or a combination of a CSTR and a PFR reactor that operates to improve yield and selectivity. Preferred embodiments of the present invention are shown in FIGS. 1-3. For example, the novel process and reactor design of the present invention advantageously enhances the yield and selectivity of a divinylarene dioxide such as DVBDO.

One embodiment of the present invention includes a process for preparing a divinylarene dioxide including the steps of:

(a) feeding one or more feed streams of the following reactants into a reactor system: (i) at least one divinylarene, (ii) at least one oxidizing agent, and (iii) at least one solvent to form a reaction mixture in the reactor system;

(b) continuously reacting together the one or more feed streams of the reactants of step (a) in the reaction mixture; and (c) controlling heat removal of the reaction mixture as the reactants of step (b) react together; wherein the heat removal is sufficient to provide a residence time of the reactants in the reaction mixture of less than about 180 minutes residence time of the reactants in the reaction step (b).

Another embodiment of the present invention includes an apparatus for continuously preparing a divinylarene dioxide including:

(A) a means for feeding one or more feed streams of the following reactants into a reactor system: (i) at least one divinylarene, (ii) at least one oxidizing agent, and (iii) at least one solvent to form a reaction mixture in the reactor system;

(B) a means for continuously reacting together the one or more feed streams of the reactants in the reaction mixture; and (C) a means for controlling heat removal of the reaction mixture as the reactants react together; wherein the heat removal is sufficient to provide a residence time of the reactants in the reaction mixture of less than about 180 minutes residence time of the reactants in the reaction.

The above apparatus may include for example one or more tubular reactors such as plug flow reactors; and/or one or more continuous stirred tank reactors comprising the reactor system.

Some of the advantages of the present invention include (1) an improved reactor design for residence time reduction for similar conversion, (2) a distributed feed for better control of reactant concentration, and (3) an effective heat removal due to enhanced surface area to volume ratio resulting in better thermal management. In addition, the reactor of the present invention can advantageously be used as a combination of continuous stirred tank reactor and plug flow reactor with or without recycle.

In addition to the above elements, the process of the present invention can be operated on a continuous platform by including a continuous vacuum distillation operation in the reaction scheme. And, the products generated in the continuous reactor of the present invention can be fed, for example, to a distillation column, such as dividing wall column (DWC), operated at suitable conditions to facilitate a one-step oxirane product (e.g., DVBDO) separation.

BRIEF DESCRIPTION OF THE DRAWINGS

For the purpose of illustrating the present invention, the following drawings show a form of the present invention which is presently preferred. However, it should be understood that the present invention is not limited to the precise arrangements and apparatuses shown in the drawings. In the accompanying drawings, like reference numerals are used to denote like parts throughout the several drawings.

FIG. 3 is schematic diagram showing an experimental or laboratory scale continuous reactor set up for synthesis of an oxirane product.

DETAILED DESCRIPTION

Figure 1:
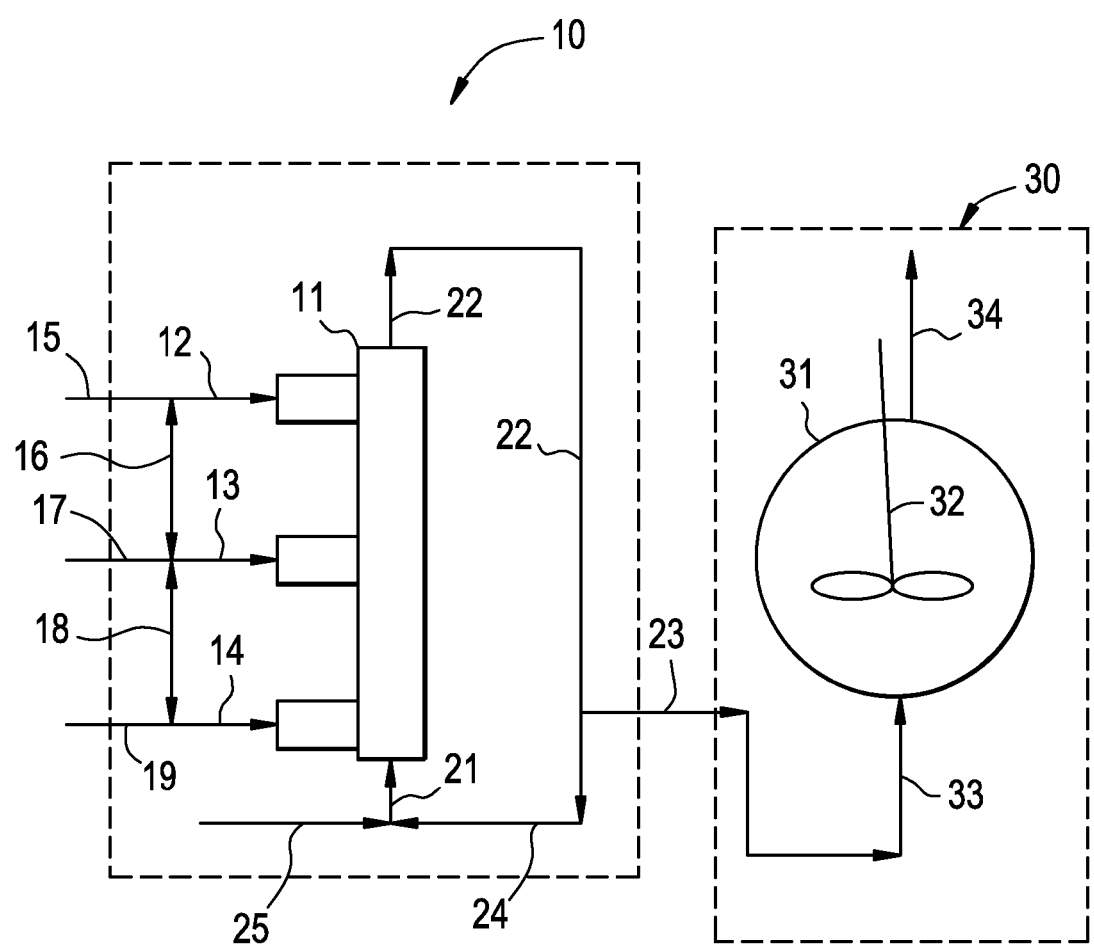
FIG. 1 is a schematic flow diagram showing one example of a reactor design and flow process of the present invention for continuous production of an oxirane product.

"Residence time" herein means the average amount of time that a process liquid spends in a system or apparatus. Residence time may be commonly calculated as liquid hold-up volume of a system divided by the rate of liquid flow through the system.

"Conversion" herein means the moles of divinyl arene converted per mole of divinylarene fed.

"Selectivity" herein means moles of divinyl arene dioxide formed per mole of divinyl arene converted.

"Percent purity (% purity)" herein means the mass concentration of a species in a process stream as measured by gel chromatography (GC), wherein the resulting measurement is expressed as a percentage.

"Stage addition" herein means a mode of reactant addition using multiple feed points in a tubular reactor or a mode of reactant addition using multiple reactors for a system comprising a series of stirred tank reactors.

"High purity" herein means greater than about 85% purity of a product. For example, the product can be a monoepoxide or a divinylarene dioxide.

As an illustration of one embodiment of the reaction(s) occurring during the process of the present invention, the following general reaction scheme shown in Reaction Scheme 1 below can occur in a reactor in accordance with the process of the present invention to yield an oxirane product such as DVBDO:

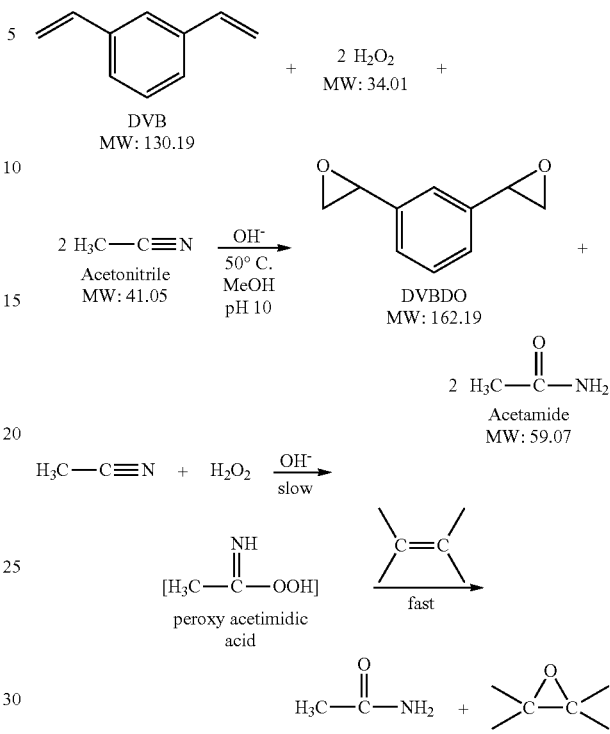

Reaction Scheme 1: Chemical Reactions Involved in Oxirane Product Synthesis

The reaction mechanism(s) shown in Reaction Scheme 1 above can involve several reactions which can be summarized as follows:

(1) A reaction can occur between hydrogen peroxide and acetonitrile in the presence of caustic to form a peroxyacetimidic acid with a rate constant $k_1$.

(2) A reaction can occur between the peroxyacetimidic acid and divinyl benzene (DVB) attacking the meta or para vinyl group on the DVB to form meta (or para) divinyl benzene monoxide with a rate constant $k_2$.

(3) A reaction can occur between the peroxyacetimidic acid and meta (or para) divinyl benzene monoxide to form divinyl benzene dioxide (DVBDO) with a rate constant $k_3$.

(4) A reaction can occur between the peroxyacetimidic acid and meta (or para) ethyl vinyl benzene to form meta (or para) ethyl vinyl benzene monoxide with a rate constant $k_4$.

In general, the above reaction mechanisms proceed through an intermediate peroxyacetimidic acid which oxidizes a divinylarene to ultimately form divinylarene dioxide. The divinylarene dioxide product, such as DVBDO product, prepared by the process of the present invention as illustrated above, can be further processed in a subsequent process operation. For example in one embodiment, the divinylarene dioxide product can be subjected to a purifying operation. The purifying operation can use, for example, a vacuum distillation or a continuous distillation process such as described with reference to FIG. 2. For example, using vacuum distillation, the divinylarene dioxide product can be purified to a desired purity level, generally up to a purity level of 95% or higher.

The reactions described above can be highly exothermic with a net heat of reaction of up to about 606 KJ/mol resulting in an adiabatic temperature rise of up to about 773 K. It is this exothermicity of the reactions that can be controlled by the process of the present invention and hence shorter residence times for the present process.

One broad embodiment of the present invention is directed to a process for preparing a divinylarene dioxide including the steps of:

(a) feeding one or more feed streams of the following reactants into a reactor system: (i) at least one divinylarene, (ii) at least one oxidizing agent, and (iii) at least one solvent to form a reaction mixture in the reactor system;

(b) continuously reacting together the one or more feed streams of the reactants of step (a) in the reaction mixture; and (c) controlling heat removal of the reaction mixture as the reactants of step (b) react together; wherein the heat removal is sufficient to provide a residence time of the reactants in the reaction mixture of less than about 180 minutes residence time of the reactants in the reaction step (b).

The reaction process of the present invention may be carried out at a predetermined temperature, a predetermined pressure, and for a predetermined period of time sufficient to produce divinylarene dioxide. The conditions of the process may vary depending on the starting reactants and raw materials used in the process.

In one embodiment of the process, the reaction is carried out continuously at a pressure and temperature sufficient to maintain the reaction composition in a single phase. Generally, the reaction can be carried out by reacting the organic feed composition and hydrogen peroxide continuously at a pressure and temperature sufficient to maintain the composition in a single phase. By "single phase" it is meant that the composition is a homogeneous single liquid system with no separate vapor phase. For example, the temperature of the reaction process may be generally from about 278 K to about 473 K in one embodiment; from about 303 K to about 343 K in another embodiment; and from about 313 K to about 333 K in still another embodiment.

Generally, the pressure of the reaction process may be from about $1.01*10^5$ Pa to about $10.1*10^5$ Pa in one embodiment, from about $1.03*10^5$ Pa to about $10.3*10^5$ Pa in another embodiment, between about $1.03*10^5$ Pa to about $5.15*10^5$ Pa in still another embodiment, and between about $1.03*10^5$ Pa to about $3.09*10^5$ Pa in yet another embodiment.

Generally, the reaction time for the overall process may be chosen between about 15 minute to about 2 hours in one embodiment, between about 15 minutes to about 1 hour in another embodiment, and between about 15 minutes to about 0.5 hours in still another embodiment. Below a period of time of about 15 minute, the time may be too short to ensure sufficient reaction under the processing conditions; and above about 2 hours, the time may be too long to be practical or economical.

The process of the present invention is carried out to maintain the reaction mixture at under basic pH conditions. For example, in one embodiment, the pH of the reaction mixture can be generally maintained in the range of from about 7 to about 12; from about 8 to about 11 in another embodiment, and from about 9 to about 11 in still another embodiment. The pH of the reaction mixture can be adjusted by feeding a pH control agent to the reaction mixture. The pH control agent can be for example sodium hydroxide, potassium hydroxide, ammonium hydroxide, calcium oxide or mixtures thereof. If the pH is less than about 7, no reaction occurs; and if the pH is greater than about 11, hydrolysis and other undesirable reactions occur. When the reaction mixture pH is maintained under basic conditions by feeding a pH controlling agent to the reaction mixture, the formation of undesired by-products is preferably minimized.

Generally, the divinylarene conversion can be in the range of from about 90 percent (%) to about 99.9% in one embodiment, from about 95% to about 99.9% in another embodiment, and from about 98% to about 99.9% in still another embodiment.

Generally, the divinylarene dioxide selectivity can be from about 40% to about 99% in one embodiment, from about 60% to about 99% in another embodiment, and from about 80% to about 99% in still another embodiment.

The steps of the present invention process includes for example, a first step of preparing the feed stream to be sent to the reactor vessel of the present invention. The feed stream can be any one of: (1) a premixed organic feed composition including an admixture of one or more of the following components: (i) at least one divinylarene compound, (ii) at least one oxidizing agent, and (iii) at least one solvent to form the premixed organic feed composition; (2) a separate and individual feed stream of each of the above components (i)-(iii); or (3) a combination of two or more feed streams of any one of the above components (i)-(iii) separately or in combination of two or more components. The feed stream or feed streams forming the organic feed composition of step (a) can be fed to a reactor of the process, for example, at near the bottom area of the reactor in one embodiment, at near the top of the reactor, at near the middle of the reactor, or a combination thereof.

In preparing the divinylarene dioxide of the present invention, the divinylarene compound, component (i), may be subjected to an epoxidation step to synthesize the product divinylarene dioxide. The divinylarene compound useful in the present invention may include for example, divinyl benzene, ethyl vinyl benzene, styrene, or any combination thereof.

One preferred embodiment of the divinylarene compound useful in the process of the present invention is described in U.S. Patent Application Publication No. US-2012-0253055-A1 published Oct. 4, 2012; and U.S. patent application Ser. No. 13/990,451 filed May 30, 2013 by Gu et al., both incorporated herein by reference.

Generally, the amount of divinylarene compound used in the process may be for example, from 1 wt % to about 30 wt % in one embodiment based on the total weight of the composition, from about 5 wt % to about 25 wt % in another embodiment; from about 10 wt % to about 20 wt % in still another embodiment; and from about 10 wt % to about 15 wt % in yet another embodiment. At a higher concentration of divinylarene compound, the by-product concentration increases; and/or the reaction exotherm may make the system unsafe.

In preparing the divinylarene dioxide of the present invention, the oxidizing agent, component (ii), may be used for epoxidizing the divinylarene compound to synthesize the product divinylarene dioxide. In one embodiment, the oxidizing agent useful in the present invention for oxidizing divinylarene to divinyl arene dioxide may include for example, a pre-prepared oxidizing agent that is added to the reaction mixture or the oxidizing agent can be a readily available compound that is added to the reaction mixture. For example, the oxidizing agent useful in the present invention may include a peroxyacetimidic acid selected, for example, from any one of hydrogen peroxide, acetonitrile, benzonitrile, propionitrile, adiponitrile or any combination thereof.

In another embodiment of the present invention, an in situ technique may be employed in forming the oxidizing agent, component (ii), and carrying out the epoxidation step of the process by (a) adding a nitrile compound and hydrogen peroxide ($H_2O_2$) to the divinylarene to be epoxidized such that a peroxycarboximidic acid is formed from the nitrile compound and $H_2O_2$ under slightly basic conditions (e.g., at a pH of at least greater than or equal to ($\geq$) about 7 as measured by a pH meter); and (b) simultaneously epoxidizing the divinylarene compound to form a divinylarene dioxide and an amide as products. In order to maintain the pH at $\geq$about 7 or more, a base may be added to the reaction mixture.

The nitrile compound employed in making the peroxycarboximidic acid in situ may be a compound in which the nitrile group is the only group capable of reacting with hydrogen peroxide. For example, especially useful nitriles may be those having the following formula:

wherein R may be a saturated hydrocarbon having from 1 to about 18 carbon atoms, preferably from 1 to about 12 carbon atoms, and more preferably from 1 to about 8 carbon atoms; or R may be an aromatic hydrocarbon having from 1 to about 18 carbon atoms, preferably from 1 to about 12 carbon atoms, and more preferably from 1 to about 8 carbon atoms; and wherein R is free of non-aromatic multiple bonds.

Generally, the amount of oxidizing agent present in the reaction mixture of the present process may be for example, from 1 wt % to about 15 wt % in one embodiment based on the total weight of the composition, from about 3 wt % to about 10 wt % in another embodiment; from about 3 wt % to about 8 wt % in still another embodiment; and from about 3 wt % to about 7 wt % in yet another embodiment.

In another embodiment, the process of the present invention can include the step of first premixing the at least one oxidizing agent and the at least one divinylarene prior to adding to the reaction mixture. The premixed components form an organic feed stream composition; and the organic feed stream composition can then be fed to the reaction mixture of step (a).

In preparing the divinylarene dioxide of the present invention, the solvent, component (iii), may be used for dissolving organic and inorganic reactants and adding a thermal mass to absorb the heat of reaction.

The solvent useful in the present invention may include water and/or one or more organic solvents suitable for the reactants. For example, aqueous solutions of hydrogen peroxide and/or basic compounds may be used in the present invention. When divinylarene compounds have a low solubility in water or are substantially water insoluble, an organic solvent for the reaction may be useful instead of, or together with, water. Alcohols, particularly water soluble alcohols, may be useful solvents, including methanol, ethanol, isopropanol, 1-methoxy-2-propanol, isobutyl alcohol, tert-butyl alcohol, or mixtures thereof. Polyhydric alcohols, for instance, ethylene glycol, 2-methyl-2,4-pentanediol, or mixtures thereof can be used as the solvent. Hydrocarbon solvents, such as for example aromatic hydrocarbon solvents including toluene, benzene, xylenes, and the like; aliphatic hydrocarbon solvents including pentane, hexane, cyclohexane, and the like; or mixtures thereof, can also be used in the present invention.

Other non-acidic solvents can be used in the present invention such as ketones, ethers, chlorinated solvents, esters, or mixtures thereof. For example, the solvents useful in the present process may include acetone, methyl ethyl ketone, 4-methyl-2-pentanone, cyclohexanone, diacetone alcohol, dimethyl ether, ethylene glycol monomethyl ether, ethylene glycol monoacetate, ethyl acetate, dioxane, methylene chloride, chloroform, or mixtures thereof. Solvents which are free from polymerizable ethylenic linkages may also be used in the present invention process.

In one preferred embodiment, the reaction solvent may comprise for example, methanol, isopropanol, diethyl ether, benzene, toluene, ethyl acetate, 4-methyl-2-pentanone, 1-methoxy-2-propanol, or mixtures thereof.

Generally, when the reaction can be carried out with predetermined amounts of liquid organic solvents, the weight ratio of the organic solvent to divinylarene may be less than about 20 in one embodiment, less than about 10 in another embodiment, and less than about 5 in yet another embodiment. In other embodiments of the present invention, the weight ratio of the organic solvent to divinylarene may be from about 0.1 to about 20.

Generally, the amount of solvent used in the process may be for example, from 30 wt % to about 70 wt % in one embodiment, from about 40 wt % to about 60 wt % in another embodiment based on the total weight of the composition; from about 45 wt % to about 55 wt % in still another embodiment; and from about 45 wt % to about 50 wt % in yet another embodiment. When a low solvent concentration is used (e.g., <30 wt %), this may (a) affect the solubility of the reactants in the solvent, and/or (b) lead to undesirable higher reactor temperature. The use of high solvent amounts (e.g., >70 wt %), may dilute the reactant stream and lead to an undesirable higher processing time and/or an undesirable larger size reactor which can result in a lower productivity process.

Another step of the process of the present invention includes (c) feeding a hydrogen peroxide feed stream into the reactor. It is necessary to employ a hydrogen peroxide feed stream in the process because the hydrogen peroxide serves as the oxidant to form the desired product divinyl benzene dioxide.

Another step of the process of the present invention may include (d) reacting continuously the organic feed composition and hydrogen peroxide at a pressure of from about $1.01*10^5$ Pa to about $10.1*10^5$ Pa in one embodiment, and at a temperature of from about 278 K to about 373 K in one embodiment.

The surface area to volume ratio of the reactor used to carry out the reaction process is such that provides a temperature control allowing the process to be operated in a continuous process. For example, generally, the surface area to volume ratio of the reactor used in the process may be for example, from 50 $m^2/m^3$ to about 2000 $m^2/m^3$ in one embodiment, from about 100 $m^2/m^3$ to about 1500 $m^2/m^3$ in another embodiment; from about 100 $m^2/m^3$ to about 1000 $m^2/m^3$ in still another embodiment; and from about 150 $m^2/m^3$ to about 800 $m^2/m^3$ in yet another embodiment.

Another embodiment of the present process, includes carrying out the process under conditions to maintain the reaction mixture at a pH in the range of from about 7 to about 12. For example, the step of the process of the present invention may include (e) maintaining the reaction at a pH in the range of from about 7 to about 12 by feeding at least one pH controlling agent to the reaction at a feed rate sufficient to maintain the desired pH of the reaction mixture. The feed addition of the pH controlling agent is such that allows the process to be operated in a continuous mode and to maintain the pH of the reaction at greater than about 7 and less than about 12.

It is necessary to maintain the pH of the reaction mixture in the above range because at a pH lower than 7, the reaction will not occur at an appreciable rate; and at a pH of greater than 12, undesirable side products can be produced. For example, the side products can include hydrolysis and methanolysis products including for example aldehyde adducts, methanol adducts, and mixtures thereof.

Generally, the pH of the reaction mixture used in the process may be, for example, from about 7 to about 12 in one embodiment, from about 8 to about 11 in another embodiment; and from about 9 to about 11 in still another embodiment.

In a preferred embodiment for preparing the divinylarene dioxide of the present invention, the pH controlling agent, component (e), can be a caustic material and the caustic material may be used to maintain the reaction mixture pH at or above 7. The caustic material useful in the present invention may include for example, hydrotalcites, sodium hydroxide, potassium hydroxide, ammonium hydroxide, magnesium hydroxide, calcium hydroxide, magnesium oxide, calcium oxide, sodium hydrogen carbonate, potassium hydrogen carbonate, Sodium Acetate Dowex strong base anion exchange resin, OH and Dowex weak base anion exchange resin, OH, or any combination thereof.

Generally, the amount of caustic material used in the process may be for example, less than about 0.1 wt % in one embodiment, from about 0.001 wt % to about 0.1 wt % in another embodiment; and from about 0.01 wt % to about 0.1 wt % in still another embodiment, based on the total weight of the composition.

In one embodiment, the reaction mixture pH is maintained in the range of from about 7 to about 12 to sustain the reaction; and to maintain the above pH range, caustic can be fed at multiple or plurality of points along the reactor length using a distributed feed configuration. For example, a multiple distributed feed configuration is shown in FIG. 1. Any of the other aforementioned suitable materials for the components (i)-(iii) can also take advantage of using the multiple distributed feed configuration as shown in FIG. 1.

Other optional compounds that may be used as feed streams to the reactor in the process of the present invention may include, for example, de-molding agents; accelerators, other solvents to lower the viscosity of the formulation further, epoxy resins, other resins such as a phenolic resin that can be blended with the epoxy, curing agents, fillers, pigments, toughening agents, flow modifiers, adhesion promoters, diluents, stabilizers, plasticizers, catalyst de-activators, flame retardants, and mixtures thereof.

Generally, the amount of other optional components, when used in the present invention, may be for example, from 0 wt % to about 99.9 wt % in one embodiment, from about 0.1 wt % to about 99.9 wt % in another embodiment; from about 1 wt % to about 99 wt % in still another embodiment; and from about 2 wt % to about 98 wt % in yet another embodiment.

In another embodiment of the process of the present invention for preparing a divinylarene dioxide, the process includes continuously feeding into a reactor vessel one or more feed materials of a divinylarene, an oxidizing agent, a solvent, and optionally a caustic compound to provide a reaction mixture inside the reactor vessel; continuously reacting the reaction mixture inside the vessel to produce a divinylarene dioxide product; continuously recovering the divinylarene dioxide product; and continuously maintaining the reaction under conditions such as to provide a divinylarene dioxide product at a conversion of greater than about 90 percent.

The one or more feed materials in the above process may be fed into the reactor vessel simultaneously or separately at two or more orifice feed points along the wall of a reactor vessel; and each of the two or more orifice feed points can be separate and apart from each other. The feed materials are fed into the reactor vessel such that (i) the feed is distributed uniformly inside the reactor vessel for better control of reactant concentration; (ii) the residence time of the feed materials in the reactor vessel is minimized; and (iii) heat removal from the reaction mixture inside the reactor vessel is maximized by enhancing the surface area to volume ratio of the reactor for better thermal management.

Another embodiment of the present invention includes a process for preparing a divinylarene dioxide including the steps of: (a) admixing (i) at least one divinylarene, (ii) at least one oxidizing agent and (iii) at least one solvent to form a premixed organic feed composition; (b) feeding the organic feed composition of step (a) to a reactor; (c) feeding a hydrogen peroxide feed stream to the reactor; (d) reacting continuously the organic feed composition and hydrogen peroxide at a pressure and temperature sufficient to maintain the composition in a single phase; and (e) maintaining the reaction at a pH sufficient to maintain the reaction under basic conditions and minimize the formation of undesired by-products by feeding at least one caustic material to the reactor or by feeding at least one catalyst to the reactor; wherein the desired divinylarene conversion and selectivity is achieved.

The preparation of the divinylarene dioxide, such as DVBDO, of the present invention using the process above, and/or any of the steps thereof, is preferably a continuous process. In order to carry out the process, a novel reactor vessel or a plurality of reactor vessels and ancillary equipment is used in the above reaction process as described herein. Thus, another broad aspect of the present invention is directed to an apparatus for continuously preparing a divinylarene dioxide.

In one general embodiment for example, the apparatus, i.e., the reactor system of the present invention, which can be operated continuously, may include one or more reactor vessels selected from: (A) a tubular reactor such as a plug flow reactor (PFR); (B) a continuous stirred tank reactor (CSTR); or (C) a combination of one or more PFRs and one or more CSTRs.

The reactor system useful in the present invention may include at least one conventional reactor vessel for example any tubular reactor well known in the art such as a plug flow reactor or any continuous stirred tank reactor well known in the art. Generally, the materials of construction of the reactor vessel may include stainless steel, or glass lined stainless steel.

Ancillary equipment for measuring the above process conditions for the process of the present invention can be used with the reactor(s) and can include for example, one or more thermocouples; one or more pressure sensors; one or more back pressure regulators; and one or more pH probes as part of a process control/monitor equipment system.

One preferred embodiment for the reactor design of the present invention may comprise, for example, a $1.6*10^{-3}$ m-$5*10^{-2}$ m diameter, of appropriate length stainless steel tube immersed in a water bath. The water bath is preferably well insulated and fitted with a submersible pump to improve convection. The water bath is preferably maintained at 323 K using an appropriate heat exchanger. A premixed organic feed including at least one solvent, at least one oxidizing agent, and DVB as described above is preferably fed at near the reactor bottom. In another embodiment, the hydrogen peroxide feed can be added along the reactor length using a distributed feed configuration.

All the feed lines are preferably maintained at a sufficient pressure to maintain the reaction. For example, generally the pressure of the reaction can be from about $1*10^5$ Pa to about $10*10^5$ Pa in one embodiment; from about $1*10^5$ Pa to about $5*10^5$ Pa in another embodiment; and from about $1*10^5$ Pa to about $2*10^5$ Pa in still another embodiment. In one illustration of the present invention, the reaction is carried out at a pressure of $1.72*10^6$ Pa. Pressure can be maintained by using a back pressure regulator known in the art.

In another embodiment, the apparatus for preparing a divinylarene dioxide includes (a) a means for continuously feeding into a reactor vessel one or more feed materials of an oxidizing agent, a divinylarene, and a pH controlling agent provide a reaction mixture inside the reactor vessel. One or more feed materials can be fed into the reactor vessel simultaneously or separately at two or more orifice feed points along the wall of a reactor vessel; and each of the two or more orifice feed points are separate and apart from each other. The feed materials can be fed into the reactor vessel such that (i) the feed is distributed uniformly inside the reactor vessel for better control of reactant concentration; (ii) the residence time of the feed materials in the reactor vessel is minimized; and (iii) heat removal from the reaction mixture inside the reactor vessel is maximized by enhancing the surface area to volume ratio for better thermal management.

The reactor system of the present invention may include one or more reactor vessels for continuously reacting the reaction mixture inside the reactor vessel(s) to produce a divinylarene dioxide product.

Once the divinylarene dioxide product is produced in the reactor vessel, a means for continuously recovering the divinylarene dioxide product produced can be included in the apparatus of the present invention.

In another embodiment, the apparatus of the present invention may include a means for continuously maintaining the reaction in the reactor vessel under conditions such as to maintain the reaction mixture at a pH in the range of from about 7 to about 12 and to provide a divinylarene dioxide product at a conversion of greater than about 90 percent.

In still another embodiment, the present invention may include an apparatus for continuously preparing a divinylarene dioxide that utilizes (A) a means for admixing one or more of the following components: (i) at least one divinylarene compound, (ii) at least one oxidizing agent, and (iii) at least one solvent to form a premixed organic feed composition;
(B) a means for feeding the premixed organic feed composition to a reactor; (C) a means for feeding a hydrogen peroxide feed stream to the reactor; (D) a means for reacting continuously the organic feed composition and the hydrogen peroxide feed stream at a pressure and temperature sufficient to maintain the composition in a single phase; and (E) a means for feeding at least one pH controlling agent to the reactor sufficient to maintain the reaction at a pH in the range of from about 9 to about 12.

With reference to FIG. 1, there is shown a schematic flow diagram of one example of a reactor design, for continuously manufacturing a divinylarene dioxide such as DVBDO, including for example a combination of a PFR generally indicated by numeral 10 and a CSTR generally indicated by numeral 30 in series.

The PFR 10 includes a tubular plug flow reactor vessel 11 with distribution feed streams 12, 13, and 14; a feed stream 21 made up of streams 24 and 25 flowing into one end of the PFR 11; and stream 22 exiting the opposite end of the PFR 11. In a preferred embodiment, the stream 22 may be further split into streams 23 and 24. The stream 23 from the PFR 11 becomes feed stream 33 which is preferably fed into the CSTR 30 which includes a CSTR vessel 31 with a stirring mechanism 32. Stream 34 exiting the CSTR 31 is a product stream 34 which can be sent to a storage unit or to one or more subsequent operating units for further processing.

In various optional embodiments, as shown in FIG. 1, feed stream 12 can be a single reactant stream 15 or a mixture of reactant streams 15 and 16; feed stream 13 can be a single reactant stream 17 or a mixture of reactant streams 16, 17 and/or 18; and feed stream 14 can be a single reactant stream 19 or a mixture of reactant streams 18 and 19. Other combinations of streams 12-19 will be apparent to one skilled in the art.

Figure 2:
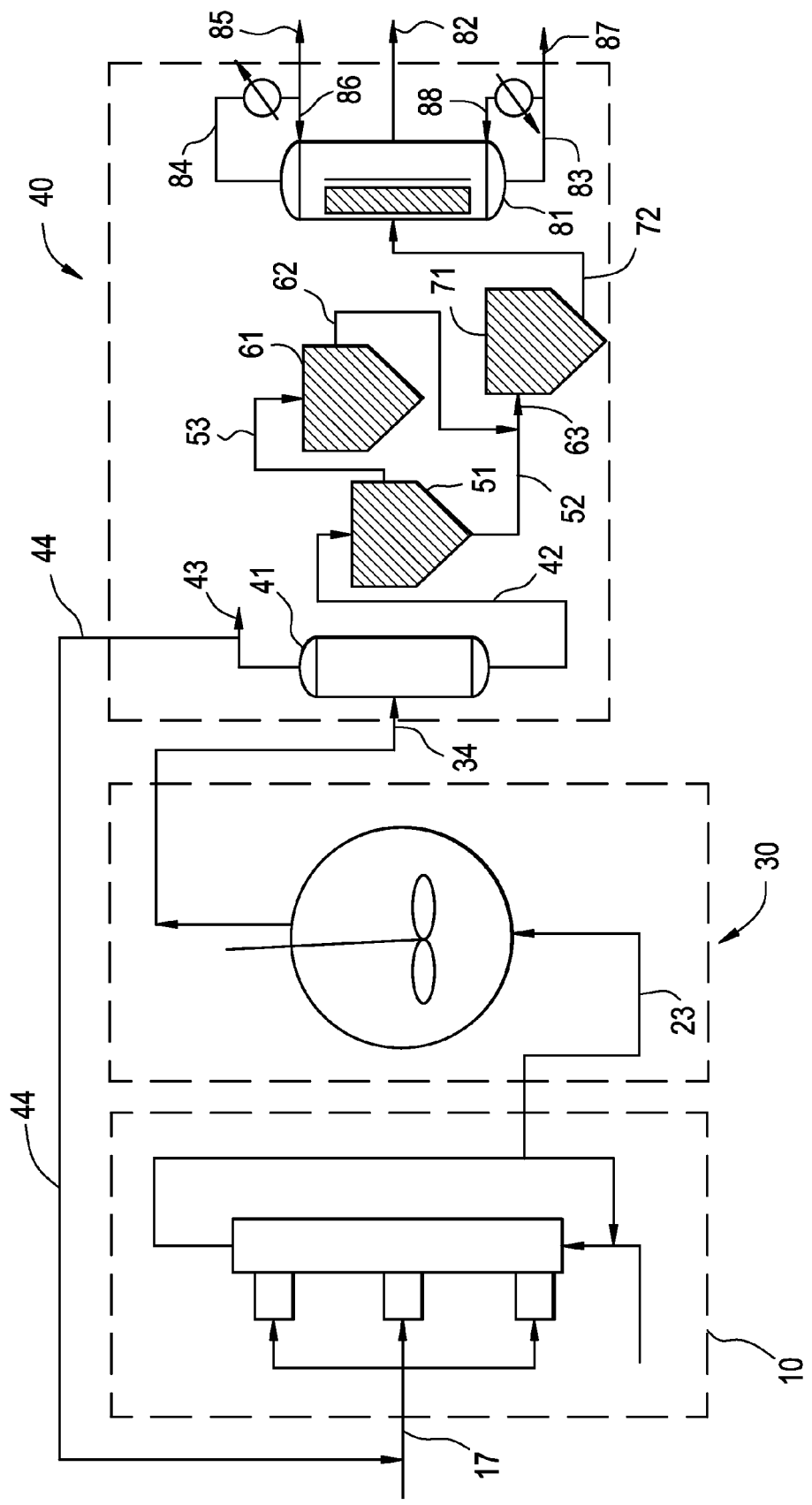
FIG. 2 is a schematic flow diagram showing an example of a continuous synthesis and purification process for producing an oxirane product and purifying the oxirane product.

With reference to FIG. 2, there is shown a schematic flow diagram of one example of a process for continuous synthesis of a divinylarene dioxide, such as DVBDO, including a PFR 10 and a CSTR 30 in series in combination with a recovery/separation system and purification process for purifying DVBDO, generally indicated by numeral 40. The process shown in FIG. 2 can be operated on a continuous platform by including a continuous vacuum distillation operation in the reaction scheme. The separation step of the process of the present invention can be carried out continuously and with a selective membrane separation. For example, the separation step may be carried out continuously and with a dividing wall column. In one embodiment, the products generated in the continuous reactor can be fed to a dividing wall column (DWC) distillation column operated at suitable conditions to facilitate a one-step DVBDO separation. The unreacted solvent and acetonitrile can be recycled to the reactor(s) to reduce the chemical footprint.

For example, as shown in FIG. 2, the product stream 34 from the CSTR 31 may comprise methanol, unreacted acetonitrile, EVBMO, DVBMO, and DVBDO and the feed stream 34 can be stripped off by, for example using a continuous distillation unit 41, as stream 42 from the solvent and acetonitrile as stream 43. At least a portion of the solvent and unreacted acetonitrile, stream 43, may be recycled to the reactor vessel 11 of the PFR 10 via recycle stream 44. The removal of solvent from stream 42 results in two phases, that is, an organic phase and an aqueous phase; and the two phases may be separated in a first decanter vessel 51. The heavier organic phase, stream 52, is removed from the bottom of the decanter 51 while the aqueous phase, stream 53, is removed from the decanter 51 from the top of the decanter 51.

The aqueous phase stream 53 from the decanter 51 can include water and acetamide; and stream 53 can be fed to a second decanter vessel 61. In decanter 61, the stream 53 can be washed with a solvent such as toluene to extract any organic products as stream 62 from the stream 53 using decanter 61.

The organic extract stream 52 from the first decanter 51 can be combined with organic stream 62 from the second decanter 61 to form a feed stream 63 flowing into a wash vessel 71. The stream 63 can be subjected to a final water wash to remove any acetamide in the organic phase of feed stream 63. The organic phase from vessel 71 can be fed as stream 72 to a dividing wall column unit 81.

In the dividing wall column 81, stream 72 can be distilled to yield a DVBDO product stream 82 as the middle component stream exiting near the middle of the dividing wall column 81. A heavies stream 83 exits column 81 near the bottom of the column 81; and a lights stream 84 also exits column 81 near the top of the column 81.

The lights stream 84 can be condensed in a condensing unit 91 to form a stream 85 exiting the column 81 and a recycle stream 86 flowing back to the column 81. The heavies stream 83 can be heated in a heating unit 92 to form a stream 87 exiting the column 81 and a recycle stream 88 flowing back to the column 81. Streams 85 and 87 can be sent to storage or can be processed further in one or more subsequent operating units.

With reference to FIG. 3, there is shown a continuous reactor set up on a laboratory scale for synthesizing a divinylarene dioxide, such as DVBDO, generally indicated as numeral 100, including an insulated vessel 110 containing water 111 to form a water bath 111, and a 0.0127 m copper coil heat exchanger 112 with heating coils 113 disposed in the water bath to keep the water 111 at a predetermined temperature. The water in the vessel 110 may be heated with the heat exchanger 112 for example up to about 50° C. Optionally, the water 111 in the vessel 110 can be stirred with a stirring means (not shown).

The reaction process of the present invention is carried out using the apparatus 100 with caustic feed streams 114, 115 and 116 pushed through tubing 130 submersed in the water 111 of the vessel 110 via pumps 121, 122, and 123, respectively. A peroxide feed stream 117 is pushed through tubing 130 submersed in the water 111 of the vessel via pump 124 and an organic feed stream 118 is pushed through tubing 130 submersed in the water 111 of the vessel via pump 125. The outgoing reaction product stream exits the water bath 111 via tubing 119.

EXAMPLES

The following examples and comparative examples further illustrate the present invention in detail but are not to be construed to limit the scope thereof.

Various terms and designations used in the following examples are explained herein below:

"DVB" stands for divinylbenzene.
"DVBDO" stands for divinylbenzene dioxide.
"EVB" stands for ethyl vinyl benzene.
"EVBMO" stands for ethyl vinyl benzene monooxide.
"DVBMO" stands for divinylbenzene monooxide.
"HPLC" stands for high pressure liquid chromatography.

Example 1

TABLE I

Typical Run Conditions for Continuous DVBDO Synthesis

| Inputs | |
|---|---|
| $H_2O_2$ solution concentration (wt %) | 35 |
| $H_2O_2$/C═C equivalent | 1.4 |
| ACN/$H_2O_2$ equivalent | 2.0 |
| MeOH/DVB | 4.0 |
| NaOH/$H_2O_2$ mole ratio | 0.020 |
| NaOH solution concentration (wt %) | 4 |
| Target temperature (° C.) | 45-50 |
| Tube length (m) | 0.6096 |
| Tube internal diameter (m) | 0.0052 |
| Target residence time (minutes) | 15 |
| Reactor surface area to volume | 19.4 |
| DVB (ml/minute) | 0.09 |
| Acetonitrile (ml/minute) | 0.17 |
| Methanol (ml/minute) | 0.43 |
| $H_2O_2$ solution (ml/minute) | 0.14 |
| 4 wt % NaOH solution (ml/minute) | 0.03 |

The reactor set up used in this Example 1 is illustrated in FIG. 3. The reactor included a $6.35*10^{-3}$ m diameter, 0.6096 m long stainless steel tube immersed in a 0.0984 cubic meter water bath which was set up in a ventilated enclosure in a laboratory. The water bath was well insulated with 0.0889 m fiber glass insulation and fitted with a Total Pond MD11300 submersible pump to improve convection. Further, the water bath was placed in a 0.208 cubic meter secondary containment for ensuring process safety. A 0.0127 m copper coil, connected to the heat exchanger (Neslab RTE 10 Thermoscientific) was immersed in the water bath to maintain the reactor at 323 K.

Premixed organic feed consisting of methanol, acetonitrile, and DVB was fed into the reactor at near the reactor bottom through a $1.58*10^{-3}$ m tube using a 500D Isco syringe pump (Teledyne Isco). The hydrogen peroxide feed was pumped through a $1.58*10^{-3}$ m passivated stainless steel tube using a 500D Isco syringe pump set at a maximum pressure of $3.45*10^6$ Pa. All the feed lines were maintained at a pressure of $1.72\ 10^6$ Pa using a back pressure regulator (Model P-788, Upchurch Scientific).

The reactor pH was maintained in the range of 9-11 to sustain the reaction by feeding caustic at three locations along the reactor length through a $1.58*10^{-3}$ m tube using 3 Gilson pumps (Model 305). The reactor temperature was monitored using a type E thermocouple (Wika Instruments). The reactor pressure was maintained at a pressure of nearly $2*10^5$ Pa using a series C fixed cracking pressure check valve (Swagelok) located at the reactor exit; and was monitored using a 0-50 psi pressure transmitter (Omega Engineering).

To begin a run sequence, the water bath was first heated by setting the chiller pump for a constant temperature bath of 50° C. Once the bath temperature reached the desired set point, a premixed organic feed of HPLC grade methanol (available from Fischer Scientific), DVB (available from Aldrich Chemicals), and HPLC grade acetonitrile (available from Fischer Scientific) was pumped through the reactor using the Isco 500D syringe pump. 1000 ppm of 4-hydroxy-2,2,6,6-tetramethylpiperidine-N-oxyl (4HT) was also added to the organic feed to prevent DVB polymerization and potential reactor plugging. Hydrogen peroxide solution (35 wt % technical grade and available from Aqua Solutions) was then flowed through the reactor. The feed samples were analyzed to ensure steady flow through the reactor. Finally, 1N sodium hydroxide was pumped through the reactor at 3 feed points at desired flow rate and the reaction was monitored for temperature and pressure. Typical feed flow rate and reaction conditions are shown in Table I.

Reaction samples were collected after nearly 30 minutes of introduction of sodium hydroxide and analyzed for residual hydrogen peroxide and pH. Samples were then periodically collected for up to 2 hours and analyzed for hydrogen peroxide conversion. At the end of the run, the caustic and hydrogen peroxide flow were stopped; heating to the water bath was shut off; and the reactor was flushed with methanol to remove any residual DVB and to prevent reactor plugging.

Initial results, shown in Table II, indicate up to 20 fold decrease in residence time from 5-6 hours to 15 minutes for comparable feed conversion of 86% and similar product composition. This improved performance can be attributed to the continuous process with better thermal management due to efficient convective heat transfer. Specifically, for a reactor surface area to volume ratio of nearly 765 m2/m3, a higher convective heat transfer is expected leading to tighter reactor temperature control; and thus, enabling higher hydrogen peroxide flow rate than that feasible in a batch process.

Further, the data described in Table II shows that computer data via Aspen model predictions for a 15 minute residence time correspond well to an experimental continuous reactor run using for example the experimental setup illustrated in FIG. 3. While the sampling time for the continuous run was 135 minutes, the total residence time for the sample was 15 minutes.

In addition, the corresponding peroxide conversion was nearly 50% and lower than the model predicted value of 99%. The over-predicted peroxide conversion is due to the kinetic model limitations since the peroxide concentration is not considered as a response variable during the kinetic parameter regression step. Hence, in the case wherein the hydrogen peroxide conversion can be over predicted, a revised model inclusive of a hydrogen peroxide response factor is recommended for accurate data prediction.

TABLE II

Data Comparison for Continuous Run with Model Predictions

| Run | Residence Time (minutes) | Conversion | | | Reaction selectivity based on DVB/EVB charged | | |
|---|---|---|---|---|---|---|---|
| | | EVB | DVB | $H_2O_2$ | EVBO | DVBMO | DVBDO |
| Aspen model | 14.3 | 69% | 88% | 99% | 69% | 45% | 42% |
| Continuous reactor (Steady state sample taken at 135 minute) | 15 | 68% | 86% | 51% | 81% | 47% | 46% |

What is claimed is:

1. A process for preparing a divinylarene dioxide comprising the steps of:
   (a) feeding one or more feed streams of the following reactants into a reactor system: (i) at least one divinylarene, (ii) at least one oxidizing agent, (iii) at least one solvent; and (iv) a pH controlling agent to form a reaction mixture in the reactor system;
   (b) continuously reacting together the one or more feed streams of the reactants of step (a) in the reaction mixture to form a divinylarene dioxide product; and
   (c) controlling heat removal of the reaction mixture as the reactants of step (b) react together via a reactor of a reactor system in step (b) having a surface area to volume ratio of greater than about 100 $m^2/m^3$; wherein the heat removal is sufficient to provide a residence time of the reactants in the reaction mixture of less than about 180 minutes residence time of the reactants in the reaction step (b)
   wherein (ii) at least one oxidizing agent comprises the reaction product of acetonitrile, hydrogen peroxide, and sodium hydroxide and is peroxyacetimidic acid;
   wherein (iii) at least one solvent comprises methanol; and
   wherein (iv) the pH controlling agent comprises sodium hydroxide.

2. The process of claim 1, including further the step of distributing the one or more feed streams of the reactants of the reaction step (b) uniformly throughout the reaction mixture in a stage addition mode.

3. The process of claim 1, wherein the surface area to volume ratio is at least about 150 $m^2/m^3$.

4. The process of claim 3, wherein the surface area to volume ratio is from about 150 $m^2/m^3$ to about 1500 $m^2/m^3$.

5. The process of claim 3, wherein the reactor used in the reaction step (b) includes at least one tubular reactor; and wherein the feed streams of the reactants of the reaction step (a) are continuously fed to the at least one tubular reactor via a distributed feed of two or more feed points located separate and apart along the wall of the at least one tubular reactor.

6. The process of claim 3, wherein the reactor used in the reaction step (b) is at least one plug flow reactor; wherein the reactor used in the reaction step (b) is at least one continuous stirred tank reactor; or wherein the reactor used in the reaction step (b) is a combination of at least one continuous stirred tank reactor and at least one plug flow reactor.

7. The process of claim 1, including further the steps of:
   (d) recycling an effluent generated in the reaction step (b) back to the reaction step (b);
   (e) continuously vacuum distilling the reaction mixture in step (b); and
   (f) separating the divinylarene dioxide product from other impurities in the reaction effluent generated in the reaction step (b).

8. The process of claim 7, wherein the divinylarene dioxide product is divinylbenzene dioxide; wherein at least one of the other impurities in the reaction effluent is divinylbenzene monooxide; and wherein the divinylbenzene monooxide is separated from the divinylbenzene dioxide in the separation step.

9. The process of claim 1, including further the step of maintaining the reaction mixture in a single phase.

10. The process of claim 1, including further the step of feeding a pH controlling agent to the reaction mixture to maintain the reaction mixture at a pH of from about 7 to about 12; and to minimize the formation of undesired by-products wherein the pH controlling agent comprises sodium hydroxide.

11. The process of claim 1, wherein the conversion of the divinylarene is in the range of from about 90 percent to about 99.9 percent; and wherein the divinylarene dioxide selectivity is from about 40 percent to about 99 percent.

12. An apparatus for preparing a divinylarene dioxide comprising:
   (a) a means for feeding one or more feed streams of the following reactants into a reactor system: (i) at least one divinylarene, (ii) at least one oxidizing agent, (iii) at least one solvent; and (iv) a pH controlling agent to form a reaction mixture in the reactor system;
   (b) a means for continuously reacting together the one or more feed streams of the reactants in the reaction mixture; and
   (c) a reactor of the reactor system for controlling heat removal of the reaction mixture as the reactants react together; wherein the reactor has a surface area to volume ratio of greater than 100 m$^2$/m$^3$ and provides a residence time of the reactants in the reaction mixture of less than about 180 minutes
wherein (ii) at least one oxidizing agent comprises the reaction product of acetonitrile, hydrogen peroxide, and sodium hydroxide and is peroxyacetimidic acid;
wherein (iii) at least one solvent comprises methanol; and
wherein the (iv) pH controlling agent comprises sodium hydroxide.

* * * * *